US011733508B2

United States Patent
Hsieh

(10) Patent No.: US 11,733,508 B2
(45) Date of Patent: Aug. 22, 2023

(54) FOOT IMPRINTING DEVICE FOR SHOWING FOOT TYPE

(71) Applicant: HOMEWAY TECHNOLOGY CO., LTD., Tainan (TW)

(72) Inventor: Chin-Hsing Hsieh, Tainan (TW)

(73) Assignee: HOMEWAY TECHNOLOGY CO., LTD., Tainan (TW)

( * ) Notice: Subject to any disclaimer, the term of this patent is extended or adjusted under 35 U.S.C. 154(b) by 399 days.

(21) Appl. No.: 17/195,951

(22) Filed: Mar. 9, 2021

(65) Prior Publication Data

US 2021/0318535 A1  Oct. 14, 2021

(30) Foreign Application Priority Data

Apr. 9, 2020 (TW) ................................ 109204134

(51) Int. Cl.
*A61B 5/107* (2006.01)
*G02B 26/00* (2006.01)
*A61B 5/103* (2006.01)

(52) U.S. Cl.
CPC .......... *G02B 26/007* (2013.01); *A61B 5/1036* (2013.01)

(58) Field of Classification Search
CPC ............................. G02B 26/07; A61B 5/1036
USPC ...................... 33/3 A, 3 B, 3 C, 3 R, 6, 512
See application file for complete search history.

(56) References Cited

U.S. PATENT DOCUMENTS

| | | | | |
|---|---|---|---|---|
| 7,051,452 | B2 * | 5/2006 | Brooks | A43D 1/025 33/227 |
| 7,337,680 | B2 * | 3/2008 | Kantro | G01L 1/247 73/862.391 |
| 7,617,068 | B2 * | 11/2009 | Tadin | A61B 5/1036 356/600 |
| 7,950,163 | B2 * | 5/2011 | Lo | A61B 5/1036 33/515 |
| 8,109,014 | B2 * | 2/2012 | Miller | A43B 13/38 36/43 |
| 8,290,739 | B2 * | 10/2012 | Tadin | A61B 5/1036 600/595 |
| 8,567,080 | B2 * | 10/2013 | Yang | A43D 1/02 33/515 |
| 10,342,473 | B1 * | 7/2019 | Berme | A61B 5/163 |
| 2011/0288446 | A1 * | 11/2011 | Hsieh | A43B 3/0042 600/592 |
| 2013/0213145 | A1 * | 8/2013 | Owings | G01L 1/225 73/862.046 |
| 2013/0296740 | A1 * | 11/2013 | Greenawalt | A61B 5/1036 600/592 |
| 2016/0302729 | A1 * | 10/2016 | Starr | A61M 60/531 |
| 2018/0177449 | A1 * | 6/2018 | Latey | A61B 5/1114 |
| 2019/0209093 | A1 * | 7/2019 | Watts | A61B 5/0077 |
| 2021/0318535 | A1 * | 10/2021 | Hsieh | A61B 5/1074 |

* cited by examiner

*Primary Examiner* — George B Bennett
(74) *Attorney, Agent, or Firm* — Muncy, Geissler, Olds & Lowe, P.C.

(57) ABSTRACT

A foot imprinting device includes a plurality of foot imprinting units each of which includes a base seat, a colored pad disposed on the base seat, and a light transmitting sheet flippably disposed on and covering the colored pad. The light transmitting sheet is movable between a first state, in which the light transmitting sheet is configured to be stepped on by a person, and a second state, in which the light transmitting sheet is configured to show a footprint of a foot of the person.

10 Claims, 9 Drawing Sheets

FOOT IMPRINTING DEVICE FOR SHOWING FOOT TYPE

CROSS-REFERENCE TO RELATED APPLICATION

This application claims priority of Taiwanese Patent Application No. 109204134, filed on Apr. 9, 2020.

FIELD

The disclosure relates to a foot imprinting device for showing the foot type of a person.

BACKGROUND

Referring to FIGS. 1 to 3, a conventional foot imprinting device for showing the foot type of a person includes a rectangular box body 11, a cover body 12 hinged to the box body 11, a rectangular ring-shaped metal frame 13 hinged between the box body 11 and the cover body 12, and a rubber sheet 14 disposed on the metal frame 14 and having a first side 141 and a second side 142 opposite to each other. The metal frame 13 together with the rubber sheet 14 is pivotable between a preparation position and a printing position. In the preparation position, as shown in FIG. 1, the metal frame 13 is located on the box body 11 and is spaced apart from the cover body 12, while the rubber sheet 14 has its first side 141 facing the box body 11 and the second side 142 facing upward. In the printing position, as shown in FIG. 2 the metal frame 13 is located on the cover body 12 and is spaced apart from the box body 11, while the rubber sheet 14 has its second side 142 facing the cover body 12 and the first side 141 facing upward.

To use the above conventional foot imprinting device, the metal frame 13 together with the rubber sheet 14 is first placed in the preparation position, after which ink is coated on the second side 142 of the rubber sheet 14, and a printing paper 15 is placed on the cover body 12. Next, the metal frame 13 together with the rubber sheet 14 is pivoted toward the cover body 12 to switch the metal frame 13 together with the rubber sheet 14 to the printing position. Then, a foot of a person steps on the first side 141 of the rubber sheet 14 to press the second side 142 of the rubber sheet 14 against the printing paper 15, thereby transferring the ink coated on the second surface 142 of the rubber sheet 14 to the printing paper 15. Thus, a footprint of the foot of the person appears on the printing paper 15.

During use of the conventional foot imprinting device, the ink and the printing paper 15 are needed, and only one foot can be printed at a time, so that it is time-consuming and inconvenient. Further, the operation of the conventional foot imprinting device is also troublesome, so that the foot of the person may be accidentally stained by the ink. Moreover, the metal frame 13 has a substantial weight, so that it is inconvenient to carry the conventional foot imprinting device. There is still room for improvement of the conventional foot imprinting device.

SUMMARY

Therefore, an object of the present disclosure is to provide an improved foot imprinting device that can alleviate at least one of the drawbacks of the prior art.

Accordingly, a foot imprinting device for showing the foot type of a person of this disclosure comprises a plurality of foot imprinting units each of which includes a base seat, a colored pad disposed on the base seat, and a light transmitting sheet flippably disposed on and covering the colored pad. The light transmitting sheet is movable between a first state, in which the light transmitting sheet is configured to be stepped on by the person, and a second state, in which the light transmitting sheet is configured to show a footprint of a foot of the person.

BRIEF DESCRIPTION OF THE DRAWINGS

Other features and advantages of the present disclosure will become apparent in the following detailed description of the embodiment with reference to the accompanying drawings, of which.

DETAILED DESCRIPTION

Figure 1:
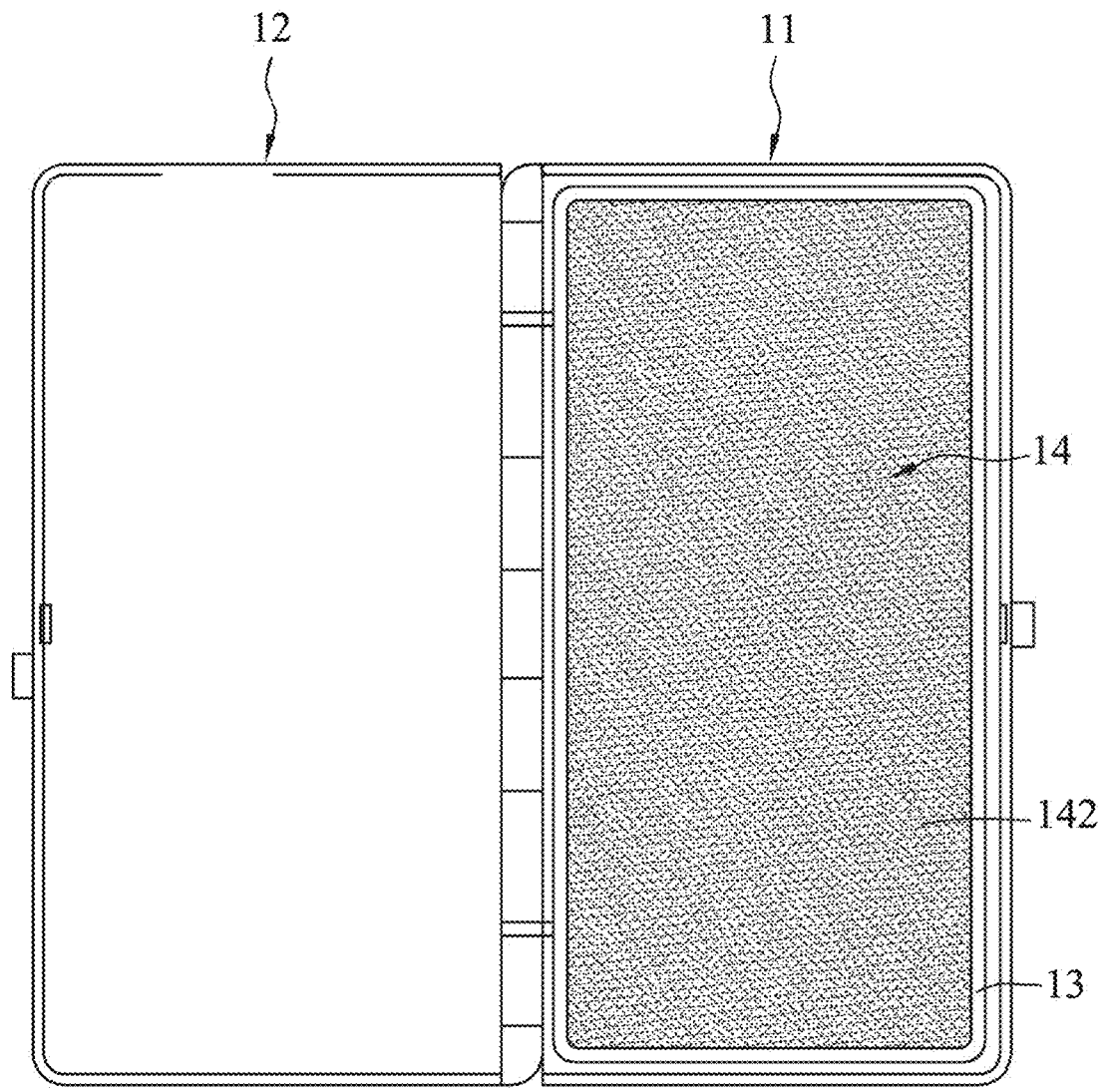
FIG. 1 is a top view of a conventional foot imprinting device.
Figure 2:
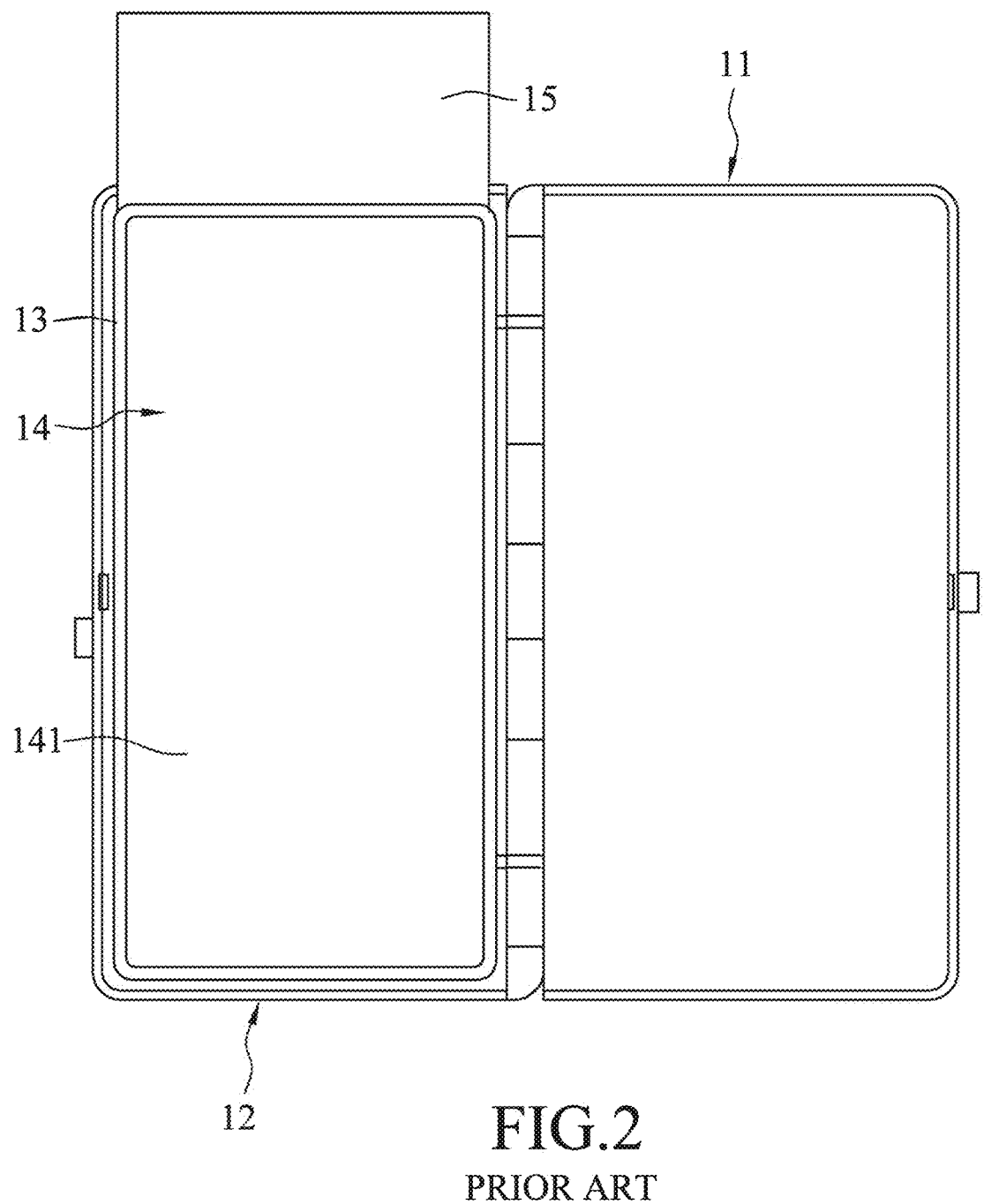
FIG. 2 is a view similar to FIG. 1, but illustrating the conventional foot imprinting device in a printing position.
Figure 3:
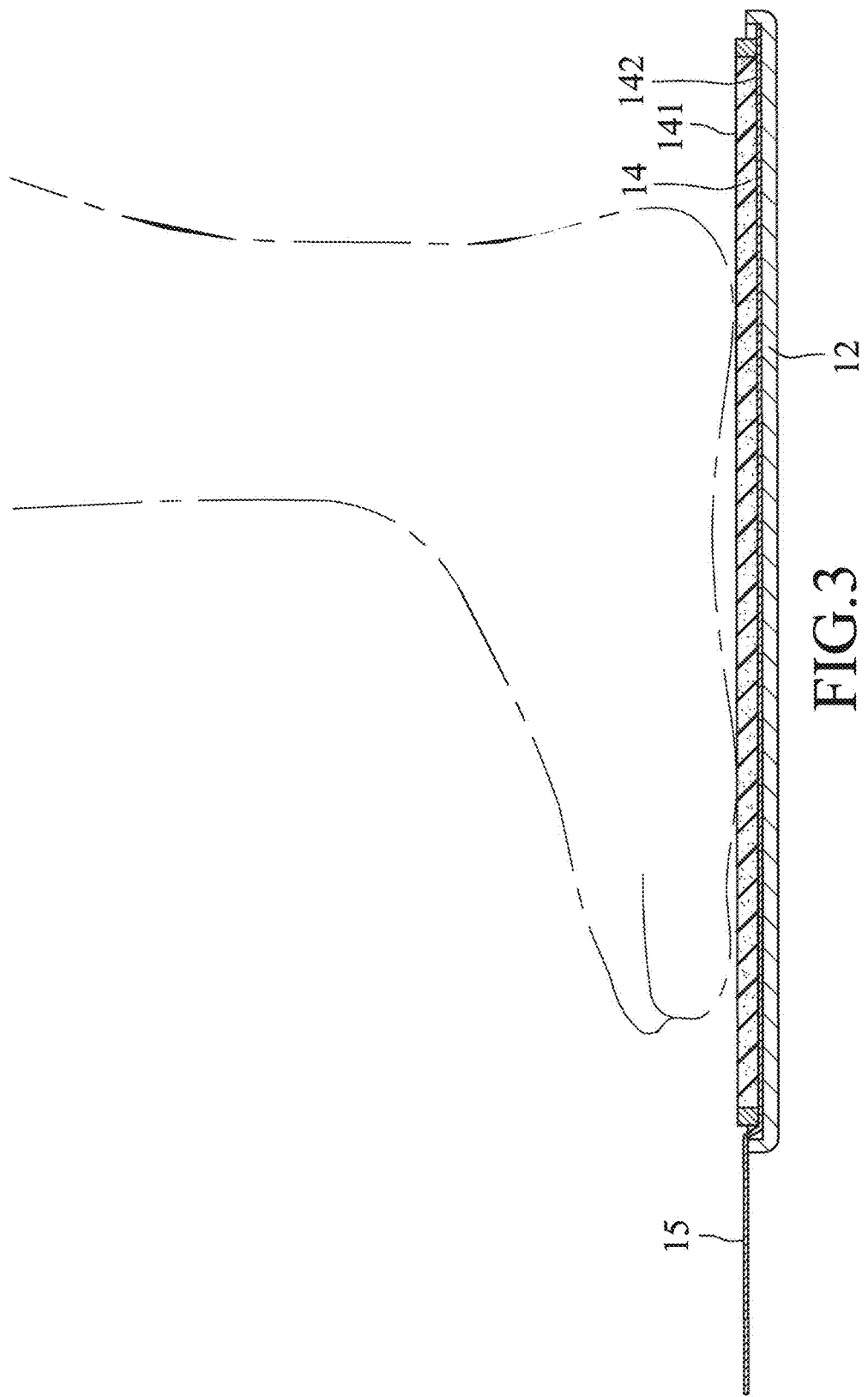
FIG. 3 is a sectional view of the conventional foot imprinting device in a state of use.
Figure 4:
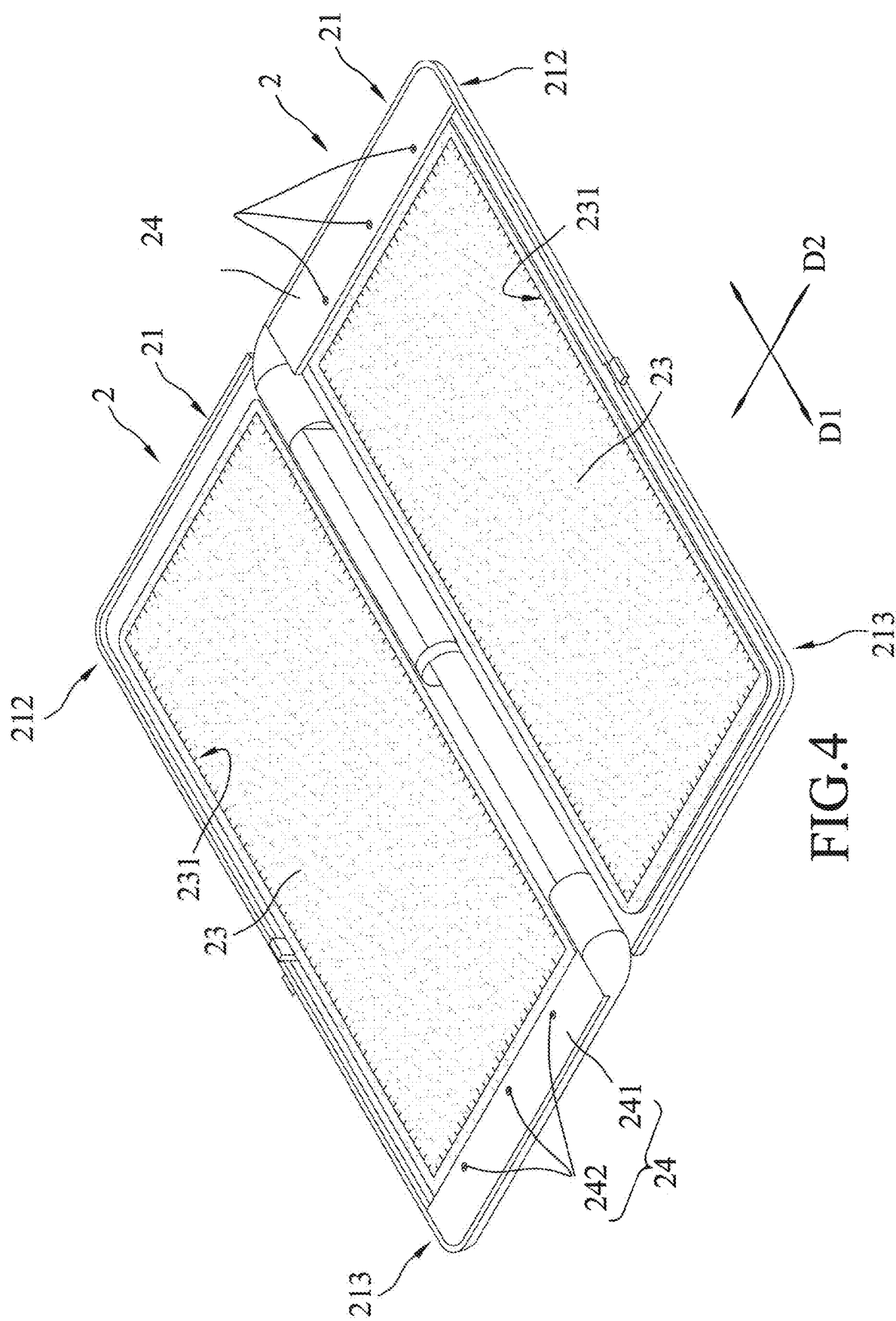
FIG. 4 is a perspective view of a foot imprinting device according to an embodiment of the present disclosure.
Figure 5:
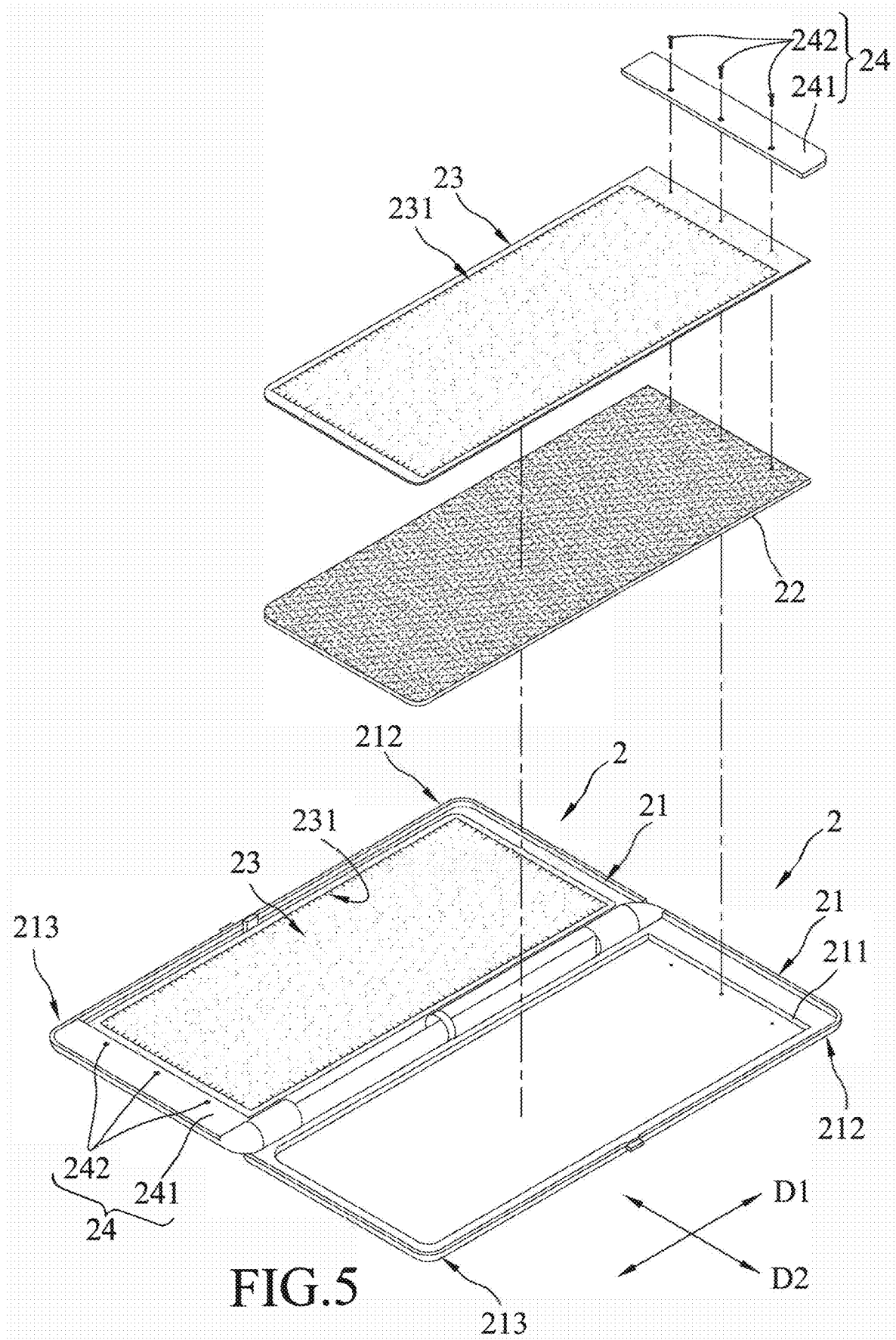
FIG. 5 is a partial exploded perspective view of the embodiment.
Figure 6:
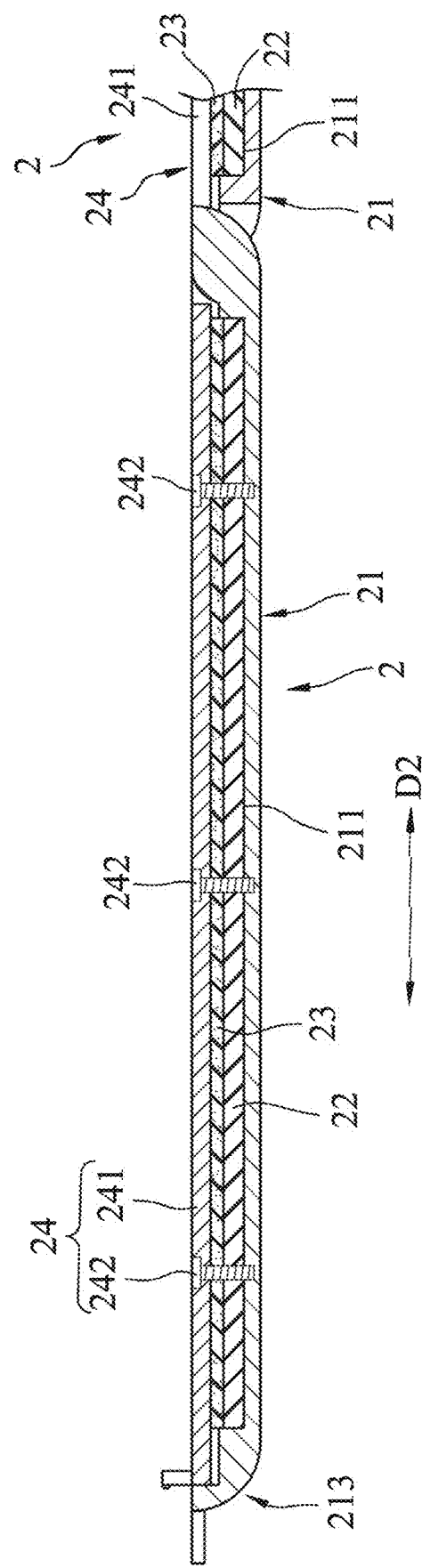
FIG. 6 is a sectional view of one of foot imprinting units of the embodiment cut along a second direction.

Referring to FIGS. 4 to 6, a foot imprinting device according to an embodiment of the present disclosure is configured for showing the foot type of a person, whether it is normal arch, flat arch or high arch. The foot imprinting device of this embodiment comprises two foot imprinting units 2. Each of the foot imprinting units 2 extends in a first direction (D1), and is hinged to the other foot imprinting unit 2 in a second direction (D2) transverse to the first direction (D1). The first direction (D1) is a length direction of each foot imprinting unit 2, while the second direction (D2) is a width direction of each foot imprinting unit 2. The foot imprinting units 2 are arranged along the second direction (D2), and are pivotable toward each other to a closed position and away from each other to an open position.

Each foot imprinting unit 2 includes a rectangular base seat 21, a colored pad 22 embedded in the base seat 21, a light transmitting sheet 23 flippably disposed on and covering the colored pad 22, and a connecting assembly 24 for fixing the colored pad 22 and the light transmitting sheet 23 to the base seat 21.

The base seat 21 is formed with a rectangular shallow groove 211 extending inwardly from an upper surface thereof, and has a first end portion 212 and a second end portion 213 opposite to each other in the first direction (D1).

The colored pad 22 has a rectangular shape, is embedded in the shallow groove 211, and is made of a dark colored soft material. In this embodiment, the colored pad 22 is made of black silicone that is non-light transmitting, and has a thickness of 1.5 mm. In other embodiment, the thickness of the colored pad 22 may be 1 to 2.5 mm.

The light transmitting sheet 23 has a rectangular shape, and is made of a light transmitting soft material. In this embodiment, the light transmitting sheet 23 is made of translucent silicone that is light transmitting. The size of the light transmitting sheet 23 is similar to that of the colored pad 22, and has a thickness of 1 mm. In other embodiment, the thickness of the light transmitting sheet 23 may be 0.1 to 2 mm. In yet another embodiment, the light transmitting sheet 23 may be completely transparent. The light transmitting sheet 23 includes a ruler scale 231 formed along a peripheral edge thereof.

The connecting assembly 24 includes a clamping member 241 for clamping the colored pad 22 and the light transmitting sheet 23 to the base seat 21, and a plurality of fasteners 242 extending through the clamping member 241, the colored pad 22 and the light transmitting sheet 23 for fastening the clamping member 241, the colored pad 22 and the light transmitting sheet 23 to the base seat 21. In this embodiment, three fasteners 242 are exemplified. The connecting assembly 24 of one of the foot imprinting units 2 is disposed on the first end portion 212 of the base seat 21 thereof, while the connecting assembly 24 of the other foot imprinting unit 2 is disposed on the second end portion 213 of the base seat 21 thereof.

Figure 7:
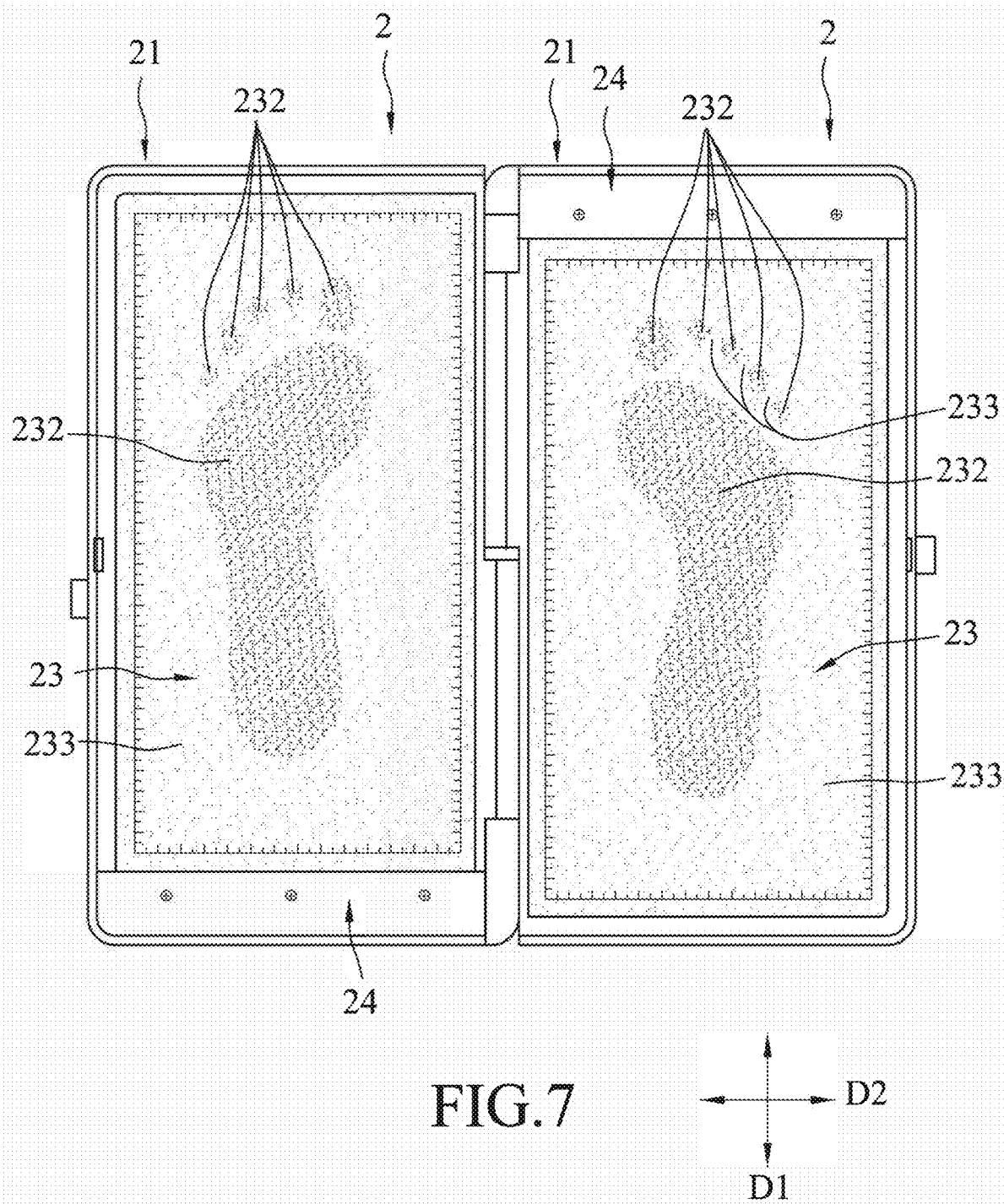
FIG. 7 is a top view of the embodiment, illustrating the effect of using the embodiment.

Referring to FIG. 7, in combination with FIGS. 4 and 6, the light transmitting sheet 23 of each foot imprinting unit 2 is movable between a first state and a second state. The second state has a degree of adhesion different from that of the first state. In the first state, as shown in FIG. 4, the dark color of the colored pad 22 can be roughly seen through the light transmitting sheet 23. When two feet of the person respectively step on the light transmitting sheets 23 of the foot imprinting units 2, the light transmitting sheets 23 are pressed against the respective colored pads 22, thereby changing the light transmitting sheets 23 from the first state to the second state. In the second state, as shown in FIG. 7, footprints of the two feet of the person are respectively shown on the light transmitting sheets 23. Further, in the second state, each light transmitting sheet 23 includes a plurality of adhesion portions 232 adhered more tightly to the respective colored pad 22 as compared to the other portions 233 thereof that are not stepped on by the person. The adhesion portions 232 cooperatively form a footprint of a corresponding one of the feet of the person.

After the footprints of the feet of the person are obtained, the size of each foot of the person can be manually determined by referring to the ruler scale 231 on each light transmitting sheet 23, and the area can be calculated to determine the type of each foot of the person, whether it is normal, flat or high arch. Further, it is also possible to photograph the light transmitting sheets 23 in the second state through the application of the mobile phone, and perform image processing on the captured image, such as cropping and binarization after normalization, to know the type of the feet of the person.

Figure 8:
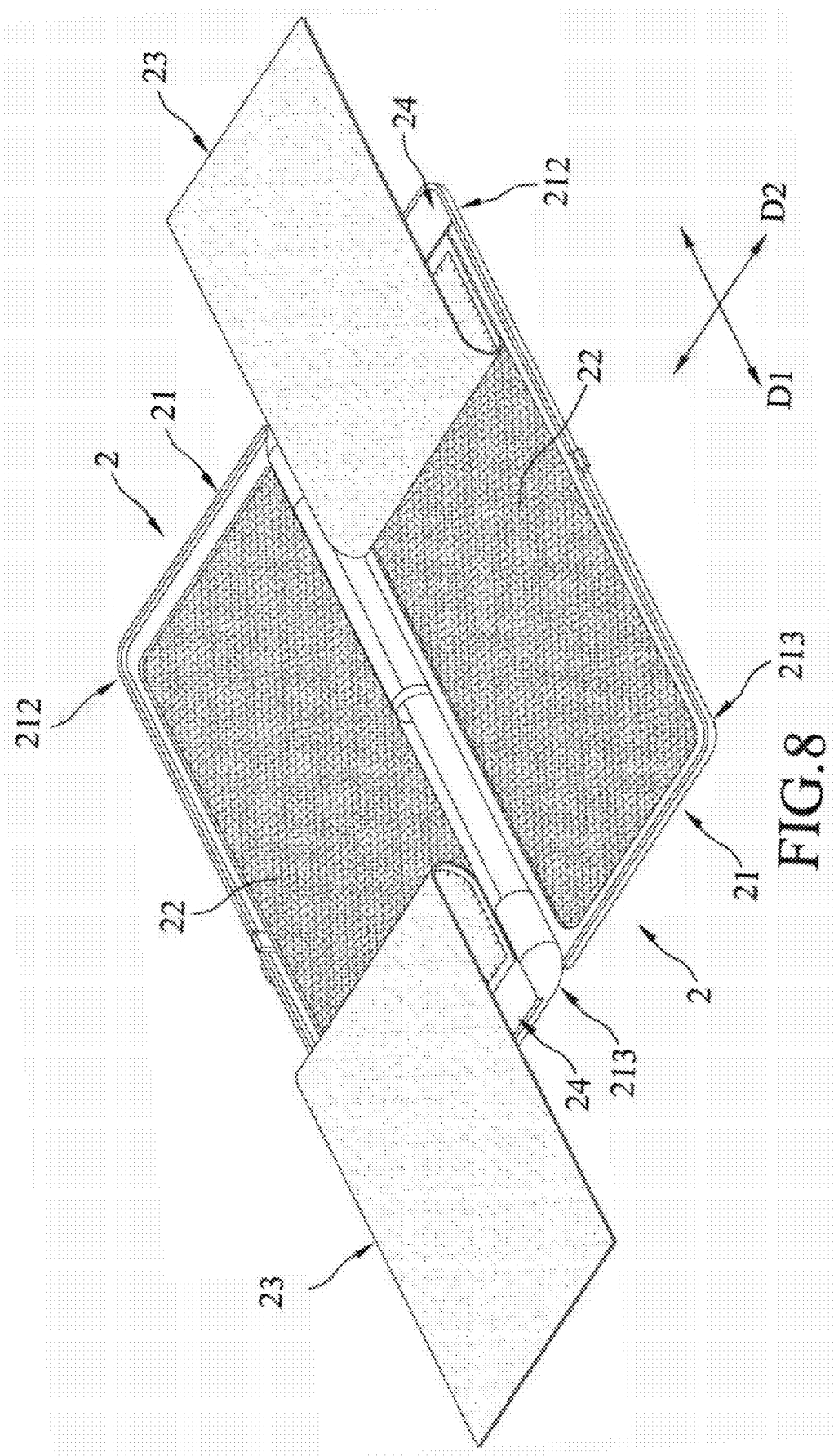
FIG. 8 is a view similar to FIG. 4, but illustrating how to use the embodiment.

Referring to FIG. 8, in combination with FIGS. 4 and 7, if it is desired to obtain the foot type of another person, each light transmitting sheet 23 is first flipped and moved away from the respective colored pad 22 along the first direction (D1) to separate the adhesion portions 232 of each light transmitting sheet 23 from the respective colored pad 22, after which each light transmitting sheet 23 is moved back on top of the respective colored pad 22, so that each light transmitting sheet 23 is switched back to the first state, as shown in FIG. 4. At this time, the feet of the another person can step on the respective light transmitting sheets 23 to know his/her foot type.

Since the connecting assembly 24 of one of the foot imprinting units 2 is disposed on the first end portion 212 of the base seat 21 of the corresponding foot imprinting unit 2, the light transmitting sheet 23 of the one of the foot imprinting units 2 is flipped and moved away from the respective colored pad 22 from the second end portion 213 to the first end portion 212 of the base seat 21 of the one of the foot imprinting units 2. On the contrary, the light transmitting sheet 23 of the other foot imprinting unit 2 is flipped and moved away from the respective colored pad 22 from the first end portion 212 to the second end portion 213 of the base seat 21 of the other foot imprinting unit 2.

Figure 9:
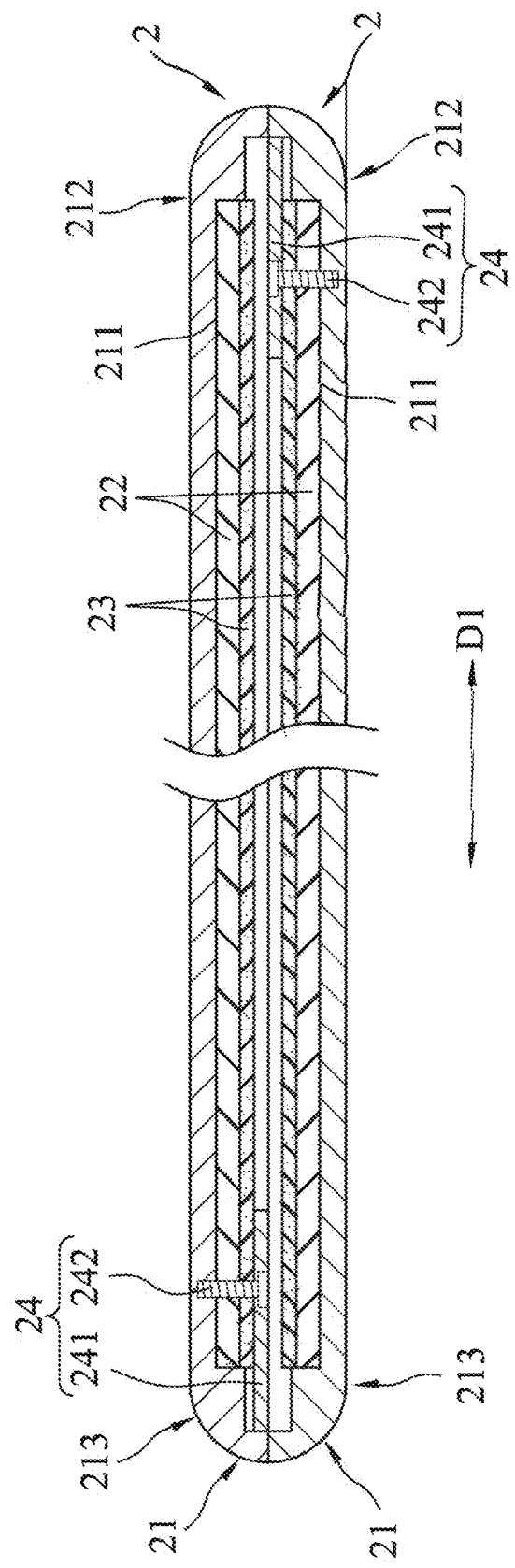
FIG. 9 is a fragmentary sectional view of foot imprinting units of the embodiment that are stacked together and that are cut along a first direction.

Referring to FIG. 9, in combination with FIGS. 5 and 7, the connecting assemblies 24 of the foot imprinting units 2 are respectively disposed on the first end portion 212 of the base seat 21 of the one of the foot imprinting units 2 and the second end portion 213 of the base seat 21 of the other foot imprinting unit 2, and are staggered relative to each other along the first direction (D1) and the second direction (D2). Through this configuration, when the foot imprinting units 2 are disposed one on top of the other along the second direction (D2), as shown in FIG. 9, the connecting assemblies 24 will not be stacked together, so that there will be no problem of a sharp increase in thickness of the foot imprinting device of this disclosure due to the superimposition of the thickness of the connecting assemblies 24.

In summary, the advantage of the foot imprinting device of this disclosure resides in that: the light transmitting sheets 23 are configured to be stepped on by the feet of the person who desires to know his/her foot type, and are movable between the first state, in which the light transmitting sheets 23 are configured to be stepped on by the feet of the person, and the second state, in which the footprints of the feet of the person are shown on the respective light transmitting sheets 23. Further, since there is no need to apply ink or use printing paper, the foot imprinting device of this disclosure can be reused by operating the light transmitting sheets 23 thereof, so that use of this disclosure is very convenient and environ-mentally friendly. Moreover, this disclosure does not include a metal frame, so that the overall weight thereof is light. Additionally, because this disclosure includes a plurality of the foot imprinting units 2, the foot type of the two feet of the user can be simultaneously known, so that use of this disclosure is economical and efficient.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A foot imprinting device for showing the foot type of a person, comprising:
   a plurality of foot imprinting units each of which includes
      a base seat;
      a colored pad disposed on said base seat; and
      a light transmitting sheet flippably disposed on said base seat and covering said colored pad, said light transmitting sheet being movable between a first state, in which said light transmitting sheet is configured to be stepped on by the person, and a second state, in which said light transmitting sheet is configured to show a footprint of a foot of the person.

2. The foot imprinting device as claimed in claim 1, wherein, when said light transmitting sheet is in the second state, said light transmitting sheet includes a plurality of adhesion portions adhered to said colored pad, and at least one other portion, and wherein adhesion of said adhesion portions to said colored pad is greater than the adhesion of said at least one other portion to said colored pad.

3. The foot imprinting device as claimed in claim 1, wherein said colored pad is made of a dark colored soft material, and said light transmitting sheet is made of one of a light transmitting and transparent soft materials.

4. The foot imprinting device as claimed in claim 3, wherein said colored pad is made of black silicone that is non-light transmitting, and said light transmitting sheet is made of translucent silicone that is light transmitting.

5. The foot imprinting device as claimed in claim 1, wherein said colored pad has a thickness of 1 to 2.5 mm, and said light transmitting sheet has a thickness of 0.1 to 2 mm.

6. The foot imprinting device as claimed in claim 1, wherein each of said foot imprinting units extends in a first direction, and said light transmitting sheet is flippable away from said colored pad along the first direction.

7. The foot imprinting device as claimed in claim 1, wherein said light transmitting sheet includes a ruler scale formed along a peripheral edge thereof.

8. The foot imprinting device as claimed in claim 1, wherein each of said foot imprinting units extends in a first direction, said base seat having a first end portion and a second end portion opposite to each other in the first direction, each of said foot imprinting units further including a connecting assembly for fixing said colored pad and said light transmitting sheet to said base seat, said connecting assembly of one of said foot imprinting units being disposed on said first end portion of said base seat of said one of said foot imprinting units, said connecting assembly of the other one of said foot imprinting units being disposed on said second end portion of said base seat of said other one of said foot imprinting units.

9. The foot imprinting device as claimed in claim 8, wherein said connecting assembly includes a clamping member for clamping said colored pad and said light transmitting sheet to said base seat, and at least one fastener for fastening said clamping member, said colored pad and said light transmitting sheet to said base seat.

10. The foot imprinting device as claimed in claim 9, wherein said plurality of said foot imprinting units includes two foot imprinting units that are arranged along a second direction transverse to the first direction and that are pivotable toward each other to a closed position and away from each other to an open position.

\* \* \* \* \*